US008927599B2

(12) United States Patent
Burgos Muñoz et al.

(10) Patent No.: US 8,927,599 B2
(45) Date of Patent: Jan. 6, 2015

(54) USE OF STATINS AS ANTICONVULSANTS, ANTIEPILEPTICS AND NEUROPROTECTORS

(75) Inventors: Javier Santos Burgos Muñoz, Armilla-Granada (ES); Carlos Ramirez Moreno, Armilla-Granada (ES); Javier Velasco Alvarez, Armilla-Granada (ES)

(73) Assignee: Neuron Biopharma, S.A., Armilla-Granada (ES)

( * ) Notice: Subject to any disclaimer, the term of this patent is extended or adjusted under 35 U.S.C. 154(b) by 535 days.

(21) Appl. No.: 12/995,816

(22) PCT Filed: Jun. 3, 2009

(86) PCT No.: PCT/ES2009/070201
§ 371 (c)(1),
(2), (4) Date: Feb. 2, 2011

(87) PCT Pub. No.: WO2009/147275
PCT Pub. Date: Dec. 10, 2009

(65) Prior Publication Data
US 2011/0184056 A1    Jul. 28, 2011

(30) Foreign Application Priority Data
Jun. 3, 2008  (ES) .................................. 200801733

(51) Int. Cl.
| A01N 43/16 | (2006.01) |
| A61K 31/35 | (2006.01) |
| C07D 309/30 | (2006.01) |
| A61K 31/40 | (2006.01) |
| A61K 31/366 | (2006.01) |

(52) U.S. Cl.
CPC ............... *A61K 31/40* (2013.01); *A61K 31/366* (2013.01)
USPC ......................................... 514/460; 549/292

(58) Field of Classification Search
USPC .......................................... 514/460; 549/292
See application file for complete search history.

(56) References Cited

U.S. PATENT DOCUMENTS

| 2004/0097593 A1* | 5/2004 | Neogi et al. .................. 514/584 |
| 2004/0176469 A1* | 9/2004 | Thomas ........................ 514/649 |

FOREIGN PATENT DOCUMENTS

WO        2007089787 A2     8/2007

OTHER PUBLICATIONS

Petanceska et al. "Statin Therapy for Alzheimer's Disease" Journal of Molecular Neuroscience, 2002, vol. 19, pp. 155-161.*
Sparrow et al. "Simvastatin Has Anti-Inflammatory and Antiatherosclerotic Activities Independent of Plasma Cholesterol Lowering" Arterioscler Thromb Vasc Biol, 2001, vol. 21, pp. 115-121.*
Vezzani et al. "Brain Inflammation in Epilepsy: Experimental and Clinical Evidence" Epilepsia, 2005, vol. 26, No. 11, pp. 1724-1743.*
Romero et al. "Lipid Peroxidation Products and antioxidants in Human Disease" Environmental Health Perspectives, Oct. 1998, vol. 106, supplement 5, pp. 1229-1234.*
Owen, Thomas "Epilesy prevention: Symptoms vs. disease" Medill Reports Chicago, Feb. 28, 2012, printed pp. 1-3.*
Johns et al. "Are HIV positive patients resistant to statin therapy?" Lipids in Health and Disease, Oct. 2007, vol. 6, pp. 1-5.*
Stix, Gary "Alzheimer's: forestalling the Darkness" Scientific American,Jun. 2010, pp. 51-57.*
Amarenco, P., M.D., et al., High-Dose Atorvastatin after Stroke or Transient Ischemic Attack, The New England Journal of Medicine, Aug. 10, 2006, pp. 549-559, vol. 355, No. 6.
Lee, J.K., et al., Statin inhibits kainic acid-induced seizure and associated inflammation and hippocampal cell death, Neuroscience Letters, 2008, pp. 260-264, vol. 440.
O'Regan, C., M.Sc., et al., Statin Therapy in Stroke Prevention: A Meta-analysis Involving 121, 000 Patients, The American Journal of Medicine, 2008, pp. 24-33, vol. 121.
Sillesen, H., et al., Atorvastatin Reduces Risk of Stroke, Cardiac Events and Endartherectomy in Patients With Carotid Stenosis: A Substudy of Sparcl, Atherosclerosis Supplements, Jun. 2007, p. 208, vol. 8, No. 1.

* cited by examiner

*Primary Examiner* — Kendra D Carter
(74) *Attorney, Agent, or Firm* — Tristan A. Fulerer; Moore & Van Allen, PLLC

(57) ABSTRACT

The use of statins as antiepileptic, anticonvulsant, neuroprotector and antioxidant compounds, potentially useful for the prevention and/or treatment of epilepsy, epileptic seizures, convulsions, neurodegenerative diseases, or diseases associated with undesired oxidation, is described.

1 Claim, 10 Drawing Sheets

USE OF STATINS AS ANTICONVULSANTS, ANTIEPILEPTICS AND NEUROPROTECTORS

CROSS-REFERENCE TO RELATED APPLICATIONS

This application is filed under the provisions of 35 U.S.C. §371 and claims the priority of International Patent Application No. PCT/ES2009/070201 filed on 3 Jun. 2009 entitled "Use of Statins as Anticonvulsants, Antiepileptics and Neuroprotectors" in the name of Javier Santos Burgos Muñoz, et al., which claims priority of Spanish Patent Application No. P200801733 filed on 3 Jun. 2008, both of which are hereby incorporated by reference herein in their entirety.

FIELD OF THE INVENTION

The invention relates to the use of statins as antiepileptic, anticonvulsant, neuroprotector and antioxidant compounds in neurodegenerative or age-associated processes, potentially useful for the prevention and/or treatment of epilepsy, epileptic seizures, convulsions, neurodegenerative diseases, or diseases associated with undesired oxidation.

BACKGROUND OF THE INVENTION

Epilepsy is a chronic disease characterized by recurrent convulsions without an apparent cause. These convulsions are transient and occur as a consequence of an excessive or synchronous neuronal activity of the brain. However, by extension, the term "epilepsy" includes a set of diseases characterized by a wide variety of symptoms, an abnormal episodic electrical activity in the brain which causes convulsions being common to all of them.

The medicaments currently used for the prevention and/or treatment of epilepsy (antiepileptics) are fundamentally based on (voltage and neuronal receptor-associated) ion channel inhibitor compounds; however, the use of such drugs causes serious side effects in the patients which affect the central nervous system such as ataxia, diplopia (double vision), motor incoordination, hyperactivity, etc., therefore it is necessary to develop new compounds useful for the treatment of epilepsy. Advantageously, the safety and efficacy of said compounds must be equal to or greater than those of the antiepileptics normally used in the treatment of epilepsy.

It has now been found that statins can be used as anticonvulsant and antiepileptic agents in the prevention and/or treatment of epilepsy, epileptic seizures and convulsions.

Statins are inhibitors of 3-hydroxy-3-methylglutaryl-coenzyme A (HMG-CoA) reductase, an enzyme which catalyzes the limiting step in cholesterol biosynthesis, and are normally used to reduce the high cholesterol levels associated with low-density lipoproteins (LDL).

The therapeutic indications of statins have been expanding over the years. In fact, these compounds are not solely used to reduce cholesterol and triglycerides levels but also used to reduce the risk of myocardial infarction and coronary death. Furthermore, new properties are being associated with statins, especially at the level of brain damage caused by trauma or in dementias. Antioxidant and anti-inflammatory properties have been proposed (Pahan, Cell Mol Life Sci. 2006; 63[10]:1165-78). Additionally, it has been demonstrated that simvastatin intensifies the memory and learning capacity in mice (Ling et al., Ann Neurol. 2006; 60[6]:729-39). Likewise, the potential use thereof as an antineoplastic agent and antiretroviral agent has been described. It has also been described that some statins prevent neuronal damage in models of acute diseases such as retinal degeneration (Nakazawa et al., J Neurochem. 2007; 100[4]:1018-31) and in trauma or ischemia (Vaughan and Delanty, Stroke 1999; 30[9]:1969-73) as well as in in vitro models of primary cortical neurons (Bosel et al., J Neurochem. 2005; 92[6]:1386-98; Zacco et al. J Neurosci. 2003; 23[35]:11104-11).

Statins are generally drugs with a high safety level as administered to reduce cholesterol and triglycerides levels in very wide pockets of the population. In fact, drugs related to the control of cholesterol and triglycerides levels represent the most successful therapeutic area worldwide, where statins represent 90% thereof, the 2 most sold drugs during the last 2 years being atorvastatin and simvastatin. Nevertheless, some statins have been withdrawn from the market as a consequence of their side effects. Thus, epileptic seizures have been documented in some cases after the administration of statins, specifically, an episode of severe rhabdomyolysis with convulsions and coma after the administration of rosuvastatin to a patient has been documented (Lorenzoni et al., Arq Neuropsiquiatr. 2007; 65[3B]:834-7); and, in another case, the administration of fluvastatin to a patient with catastrophic antiphospholipid syndrome caused focal convulsions (Miesbach et al., J Neurol Sci. 2005; 238[1-2]:93-5).

SUMMARY OF THE INVENTION

The inventors have now found that a statin, such as simvastatin, surprisingly has antiepileptic and anticonvulsant properties (Examples 1-3), exerts a protective effect against death caused by an excitotoxic substance (Example 4), as well as a protective effect against neuronal death in the hippocampus caused by an excitotoxic substance (Example 5), and a neuroprotective effect against neurodegeneration, apoptosis and reactive gliosis, caused by an excitotoxic substance (Examples 6-8), and, furthermore, exerts an antioxidant effect against lipid peroxidation caused by an excitotoxic substance (Example 9). Likewise, the inventors have also found that other statin, specifically lovastatin, also has antiepileptic and anticonvulsant properties against the action of an excitotoxic substance (Example 10).

Said examples show the potential use of statins in the prevention and/or treatment of epilepsy and convulsive seizures or convulsions, as well as their capacity to protect from neuronal death associated with neurodegenerative diseases in deep regions of the brain such as the hippocampus. Furthermore, and, surprisingly, the present invention shows for the first time in vivo that statins are anti-excitotoxic agents, showing their protective capacity against the excitotoxic syndrome associated with different chronic neurodegenerative diseases (e.g., Alzheimer's disease, Parkinson's disease, multiple sclerosis, amyotrophic lateral sclerosis, status epilepticus, Huntington's disease, etc.).

Therefore, the present invention relates to the use of statins as (i) antiepileptic agents, (ii) anticonvulsant agents, (iii) neuroprotector agents, particularly, neuroprotector agents against chronic neurodegenerative diseases (e.g., Alzheimer's disease, Parkinson's disease, multiple sclerosis, amyotrophic lateral sclerosis, status epilepticus, Huntington's disease, etc.), more specifically, neuroprotector agents against the excitotoxic syndrome associated with said chronic neurodegenerative diseases, as well as neuroprotector agents against apoptosis and reactive gliosis, caused by excitotoxic substances, (iv) antiapoptotic agents, and (v) antioxidant agents in neurodegenerative or age-associated processes.

The results obtained can be extrapolated for prophylactic or therapeutic purposes for their application on the population at risk. Likewise, due to the fact that statins are generally rather safe compounds, with a relatively low toxicity profile, their use as a drug is very suitable and does not require complex clinical trials as occurs with other drug candidates where the toxicity and safety of which are unknown.

Therefore, in one aspect, the invention relates to the use of a statin in the preparation of a pharmaceutical composition for the prevention and/or treatment of epilepsy, epileptic seizures, convulsions, neurodegenerative diseases, or diseases associated with undesired oxidation.

In another aspect, the invention relates to a statin for the prevention and/or treatment of epilepsy, epileptic seizures, convulsions, neurodegenerative diseases, or diseases associated with undesired oxidation.

In another aspect, the invention relates to a method for the prevention and/or treatment of epilepsy, epileptic seizures, convulsions, neurodegenerative diseases, or diseases associated with undesired oxidation, in a subject in need of treatment, which comprises the administration of a therapeutically effective amount of a statin to said subject.

DETAILED DESCRIPTION OF THE INVENTION

Definitions

Figure 1:
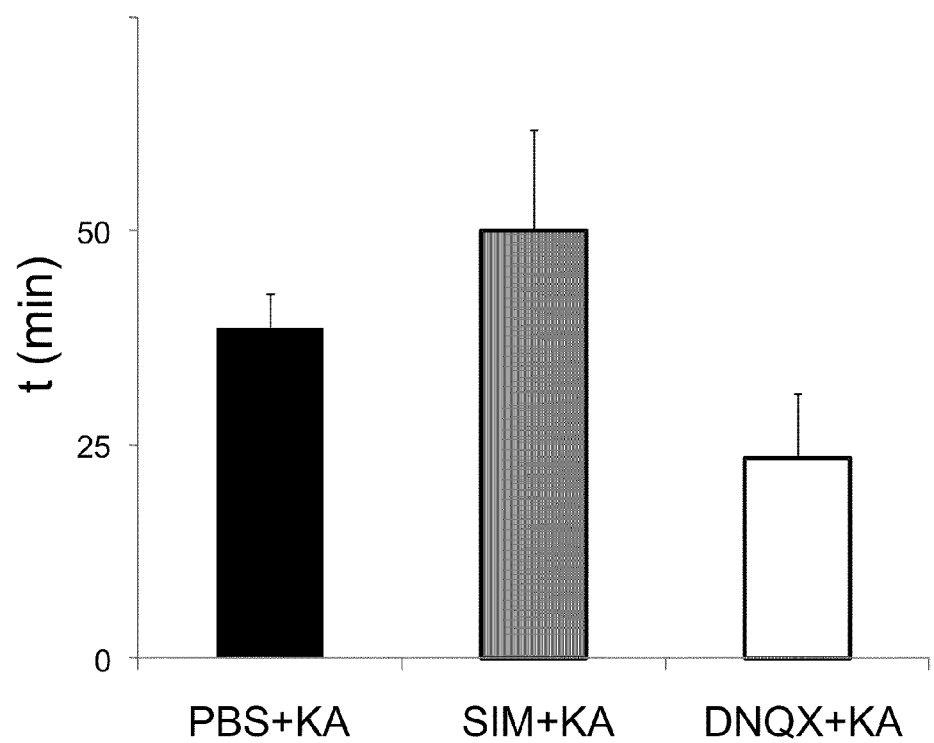
FIG. 1 is a bar graph depicting the latency time at the start of the convulsions in animals with different treatments. The graph shows the post-administration time of the epileptic agent at which the first convulsion occurs according to the treatment.

To aid in understanding the invention object of this patent application, the meaning of several terms and expressions used in the context of the invention is set forth below.

The term "statin", as it is used herein, relates to an inhibitor of 3-hydroxy-3-methylglutaryl-coenzyme A (HMG-CoA) reductase enzyme, which catalyzes the limiting step of cholesterol biosynthesis and includes any natural, synthetic or semi-synthetic, known or newly synthesized or newly designed statin or related molecules; as it is used herein, the term statin-"related molecules" refers to those molecules with hypolipidemic (hypocholesterolemic or hypotriglyceridemic) capacity. Non-limiting illustrative examples of statins which can be used in the context of the present invention include atorvastatin, cerivastatin, fluvastatin, lovastatin, mevastatin, a monacolin (e.g., monacolin M, monacolin J, monacolin N, monacolin L, monacolin X, etc.), pitavastatin (also known as itavastatin), pravastatin, rosuvastatin, simvastatin, etc., as well as combinations of any two or more statins, for example, monacolins, for example, monacolin M, monacolin J, monacolin N, monacolin L, monacolin X, etc., or any other combination of any two or more statins. Some statins can be in the closed form (lactone) or in the open form (hydroxy acid). Hydroxy acids (open form) can be prepared from the corresponding lactones by conventional hydrolysis, for example, with sodium hydroxide in methanol, sodium hydroxide in tetrahydrofuran-water and the like.

In the open form (hydroxy acid), the statins react to form salts with cations of metals and amines, which are pharmaceutically acceptable, formed from organic or inorganic bases. The term "pharmaceutically acceptable" means that the compound is physiologically tolerable and generally does not cause an allergic reaction or a similar unfavorable reaction, such as a gastric disorder, dizziness or the like, when administered to a subject; said term "pharmaceutically acceptable" preferably means approved by a government regulatory agency or listed in the United States Pharmacopoeia or in another generally recognized pharmacopoeia for use in animals (e.g., European Pharmacopoeia, etc.). The term "pharmaceutically acceptable metal salt" contemplates salts formed with sodium, potassium, calcium, magnesium, aluminum, iron and zinc ions. The term "pharmaceutically acceptable amine salt" contemplates salts with ammonia and organic nitrogen bases strong enough to form salts with carboxylic acids. The pharmaceutically acceptable salts of the statins can differ from the corresponding free acids in several physical characteristics such as solubility and melting point, but they are considered equivalent to the free acid form for the purposes of this invention. The free open form (hydroxy acid) of the statins can be regenerated from the salt form, if desired, by contacting the salt with a diluted aqueous solution of an acid such as hydrochloric acid and the like.

The closed form (lactone) of the statins can be regenerated by dissolving the open form (hydroxy acid) in an inert solvent such as, for example, toluene, benzene, ethyl acetate and the like, at temperatures comprised between approximately 0° C. and approximately the boiling point of the solvent, typically (although not necessarily) with simultaneous separation of the resulting water and catalysis with strong acids, e.g., hydrochloric acid and the like.

Likewise, the statins can exist in a solvated or non-solvated form and such forms are equivalent to the non-solvated form for the purposes of this invention.

Consequently, both the closed forms (lactones) and the open forms (hydroxy acids) of statins, either in free acid or pharmaceutically acceptable form, solvated or non-solvated, fall within the scope of the definition of statin as used in the present description.

The term "epilepsy", as it is used herein, relates to a chronic brain syndrome having varied causes, characterized by recurrent seizures due to excessive hypersynchronic discharges of nervous impulses by the neurons, possibly associated with several clinical and paraclinical manifestations. The seizures can be convulsive or non-convulsive. Epilepsy can have many causes; in some cases it can be due to different types of brain injuries (e.g., brain traumas, sequelae of meningitis, tumors, etc.); in other cases there is no injury but a genetic predisposition to seizures; in other cases, the etiology of the epilepsy can be environmental, due to pharmacological treatments, due to excitotoxicity, trauma, stress processes, aging, development problems, neurological diseases, psychological crises, problems during gestation, problems during labor, etc.

The term "epileptic or convulsant", as it is used herein, relates to any epileptic seizure or convulsion of any etiology, for example, genetic, environmental, due to pharmacological treatments, due to excitotoxicity, due to trauma, due to stress processes, due to aging, due to development problems, due to neurological diseases, due to psychological crises, due to problems during gestation, due to problems during labor, etc. An epileptic seizure occurs when an abnormal electrical activity in the brain causes an involuntary change of body movement or function, feeling, in the capacity of being alert or in behavior, and can be partial or generalized (convulsive or non-convulsive).

The term "antiepileptic or anticonvulsant", as it is used herein, relates to the attenuation of the epileptic seizures or convulsions, for example, in the duration and/or the intensity, or to the disappearance of the epileptic seizures or convulsions, or to the reduction or disappearance of the side effects thereof.

The term "neurodegenerative disease", as it is used herein, includes diseases which result from the degeneration or deterioration of nervous tissue, particularly of neurons, leading over time to a dysfunction or to a disability; the term degeneration includes loss of cell viability, loss of cell function and/or loss of the number of cells (neurons or others). Illustrative, non-limiting, examples of neurodegenerative diseases include Alzheimer's disease, Huntington's disease, Parkinson's disease, amyotrophic lateral sclerosis (ALS), multiple sclerosis, etc. In a particular embodiment, said neurodegenerative disease is a disease related to neuronal death caused by an excitotoxic substance, for example, neuronal death in the hippocampus caused by an excitotoxic substance.

The term "neuroprotective", as it is used herein, relates to the attenuation of the effects of neuronal degeneration or death by means of any mechanism known or to be known, for example, necrosis, apoptosis, autophagia, oxidative damage, deposition of byproducts, loss of cell architecture, etc., or to the disappearance of the effects of neuronal degeneration or death by means of any mechanism known or to be known, for example, necrosis, apoptosis, autophagia, oxidative damage, deposition of byproducts, loss of cell architecture, etc., or to the reduction or disappearance of the side effects thereof.

The term "disease associated with undesired oxidation", as it is used herein, relates to a disease caused by undesired oxidation (e.g., excessive oxidation) or in which said undesired oxidation is a symptom. Said undesired oxidation can be the consequence of the damage caused by free radicals to proteins, DNA and/or lipids independently of the specific free radical involved or of the target. Undesired oxidation involves an excessive generation of free radicals which can cause a dysfunction in cells, tissues or organs and can therefore form a potential mechanism of a disease. In a particular embodiment, said undesired oxidation can be caused by age (aging) or by a neurodegenerative process and can cause by itself or in combination with other factors the onset of several diseases. In a specific embodiment, said undesired oxidation relates to the oxidative damage by lipid peroxidation caused by an excitotoxic substance.

The term "subject", as it is used herein, relates to a member of a mammal species and includes but is not limited to domestic animals, primates and humans; preferably, the subject is a male or female human being of any age or race. In a particular embodiment, said subject is a mammal which suffers or is susceptible to suffering from epilepsy, epileptic seizures, convulsions, or a neurodegenerative disease, such as a chronic neurodegenerative disease.

New Therapeutic Uses of Statins

In one aspect, the invention relates to the use of a statin in the preparation of a pharmaceutical composition for the prevention and/or treatment of:
a) epilepsy,
b) epileptic seizures,
c) convulsions,
d) neurodegenerative diseases, or
e) diseases associated with an undesired oxidation.

Virtually any statin, both natural and synthetic or semisynthetic, known or newly synthesized or newly designed, or a related molecule, can be used to put the present invention into practice. The invention contemplates both the use of a single statin and of a mixture of two or more statins. In a particular embodiment, said statin is selected from the group consisting of atorvastatin, cerivastatin, fluvastatin, lovastatin, mevastatin, monacolin, pitavastatin, pravastatin, rosuvastatin, simvastatin, the pharmaceutically acceptable salts thereof, and the mixtures thereof. For the sake of simplicity, the term "monacolin" relates to any of the isolated monacolins (monacolin M, monacolin J, monacolin N, monacolin L, monacolin X, etc.) as well as the mixtures of two or more of said monacolins. In a particular embodiment, said statin is simvastatin.

The previously mentioned statins are commercially available known compounds, or they can be obtained by conventional methods, for example by means of fermentation (e.g., lovastatin, mevastatin, pravastatin, simvastatin, etc.) or by means of synthesis (e.g., atorvastatin, cerivastatin, fluvastatin, pitavastatin, rosuvastatin, etc.), as described in, for example, EP 409281, EP 325130, WO 84/02131, U.S. Pat. Nos. 4,231,938, 3,983,140, 4,346,227 and EP 33538.

A number of assays performed by the inventors have shown the antiepileptic effect of a statin (e.g., simvastatin, lovastatin) against the action of an excitotoxic substance, as well as its neuroprotective effect in the neurons of the hippocampus, and its antioxidant effect in regions of the cerebral cortex as it prevents the oxidative damage by lipid peroxidation due to the action of an excitotoxic substance.

Figure 12:
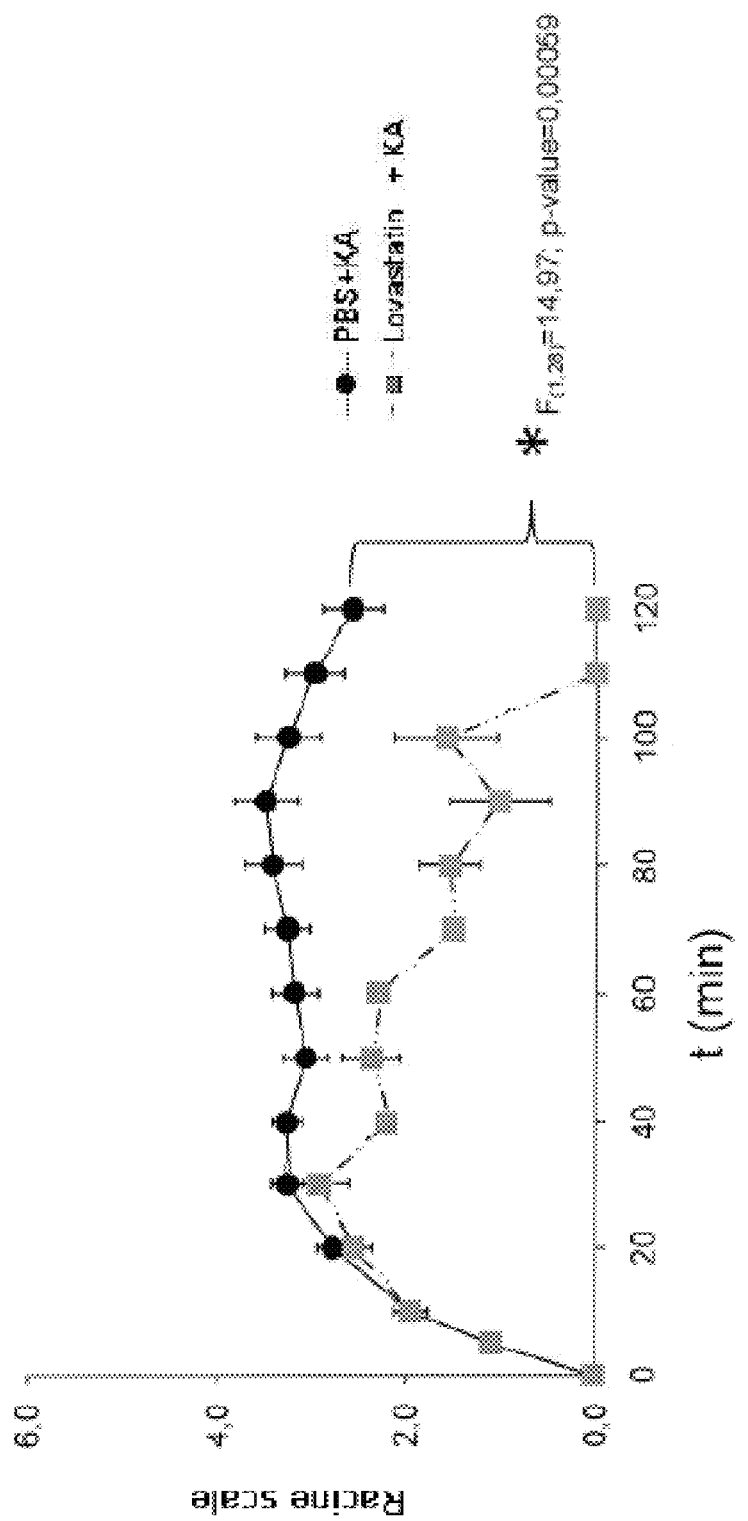
FIG. 12 is an XY scatter chart depicting the severity level of the epileptogenic score observed according to the Racine scale (Racine, Electroencephalogr Clin Neurophysiol 1972; 32[3]:281-94) versus the post-inoculation time of the epileptogenic substance (kainic acid or kainate or KA). The graph shows the evolution of the epileptogenic score of the animals according to the treatment received: PBS or lovastatin. The data were statistically analyzed by means of the ANOVA test for the general variance between groups for the entire observation time (*p-value<0.05).

The antiepileptic effect of simvastatin against the action of an excitotoxic substance (kainate) is described in Examples 1-3. In said examples, it was observed that the time period of the onset of the first convulsion (latency) in the animals to which the excitotoxic substance and the statin (simvastatin) had been administered was longer than in the rest of the treatments (FIG. 1), which demonstrates the antiepileptic or anticonvulsive effect of said statin. Likewise, the antiepileptic effect of lovastatin against the action of kainate is described in Example 10 and FIG. 12, where it can be seen that after the inoculation of kainate there was an increase of the epilepsy levels until 50-60 m.p.i. and, after that time, a progressive decrease was observed in the severity of the symptoms of the group treated with lovastatin, unlike the group to which PBS had been administered, in which the epileptic levels continued to increase until 90 m.p.i. The treatment with lovastatin completely reduced the epilepsy symptoms caused by KA at the end of the observation time, whereas the PBS+KA group maintained levels of about 3 at the end of the experiment.

Likewise, as is known, the severity of the convulsions and the chain effect of excitotoxicity induces, in some cases, the death of the animal; for this reason, the inventors analyzed if the antiepileptic effect of the statin (e.g., simvastatin) was accompanied by a reduction of the mortality caused by an excitotoxic substance (Example 4). In the results obtained (FIG. 6), a higher survival index is observed in the mice treated with simvastatin with respect to those treated with PBS, which indicates that the treatment with said statin (simvastatin) protects the animals from death due to convulsions and to the rest of the organic effects caused by an excitotoxic substance.

Given that the severity of epileptic symptoms has a direct correlation with neuronal death and the destructuring of specific regions, for example, the hippocampus, the inventors analyzed if the antiepileptic and protective effect of said statin (simvastatin) was accompanied by a reduction of those effects at cell level caused by an excitotoxic substance (Example 5). The results obtained (FIG. 7) show that there is evidence of neuronal death in the hippocampus both in the group of animals treated with PBS and KA (PBS+KA) and in the group of animals treated with said statin (simvastatin) and KA (SIM+KA); however, in the group of animals treated with simvastatin said evidence is restricted to a specific region (CA2 region) whereas a more general destructuring of the hippocampus is observed in the group of animals treated with placebo (PBS), evidence of neuronal death being observed in several regions: CA1, CA2, CA3 and dentate gyrus. These results show the protective effect (capacity to minimize the effects of neuronal damage) of said statin (simvastatin) against the neuronal death in the hippocampus caused by an excitotoxic substance.

For the purpose of better defining the neuroprotective effect of simvastatin, the inventors analyzed in more detail the neurodegenerative process which was occurring in the neurons of the hippocampus and the effect that the treatment with said statin had thereon (Example 6). The results obtained (FIG. 8) illustrate that the treatment with simvastatin (SIM+KA) qualitatively reduces the number of degenerating neurons in the hippocampus, which shows the neuroprotective capacity of said statin (simvastatin) against the neurodegeneration caused by an excitotoxic substance.

Likewise, for the purpose of analyzing the protective capacity of simvastatin against death by apoptosis, the inventors analyzed the effect exerted by the treatment with a statin (simvastatin) on neuronal death by apoptosis in the neurons of the hippocampus caused by an excitotoxic substance (Example 7). The results obtained (FIG. 9) show that the treatment with simvastatin qualitatively reduces the number of neurons in apoptosis and that the positive labeling for apoptosis in the group of animals treated with simvastatin (SIM+KA) is exclusively restricted to the CA2 region of the hippocampus, whereas in other groups of animals a larger number of neurons in apoptosis is observed in the CA1, CA2, CA3 and dentate gyrus regions, the protective capacity of said statin (simvastatin) against the neuronal death by apoptosis caused by the administration of an excitotoxic substance thus being verified.

Furthermore, for the purpose of determining if the protective capacity of said statin (simvastatin) had a global effect, the inventors analyzed other histopathological labels indicating neuronal damage, specifically, the reactive gliosis caused in the hippocampus by an excitotoxic substance and the effect that the treatment with said statin had thereon (Example 8). The results obtained (FIG. 10) show that the treatment with said statin (simvastatin) qualitatively reduces the astrocytic activation in the neuropil of the hippocampus as well as the presence of astrocytes in this region of the hippocampus, which demonstrates, in combination with the previous results, the neuroprotective capacity of said statin (simvastatin) against the effects of the administration of an excitotoxic substance.

Finally, for the purpose of determining if the neuroprotective capacity of statins (e.g., simvastatin) also included an antioxidant effect, the inventors analyzed the effect that the treatment with said statin (simvastatin) had on the lipid peroxidation induced by an excitotoxic substance (Example 9). The results obtained (FIG. 11) illustrate that the treatment with said statin (simvastatin) qualitatively reduces the number of labeled neurons and the intensity of the HNE signal, which shows that said statin (simvastatin) has, in addition to a neuroprotective effect in the neurons of the hippocampus, an antioxidant effect in regions of the cerebral cortex since it prevents the oxidative damage by lipid peroxidation due to the action of an excitotoxic substance.

For its administration in the prevention and/or treatment of epilepsy, epileptic seizures, convulsions, neurodegenerative diseases, or diseases associated with undesired oxidation, the statin will be formulated in a pharmaceutical composition, in a therapeutically effective amount, together with or more pharmaceutically acceptable vehicles or excipients.

The pharmaceutical composition provided by this invention can contain one or more different statins together with one or more pharmaceutically acceptable vehicles or excipients. In a particular embodiment, said pharmaceutical composition comprises a single statin. In another particular embodiment, said pharmaceutical composition comprises two or more statins. Said pharmaceutical composition is useful for the treatment of epilepsy, epileptic seizures, convulsions, neurodegenerative diseases, or diseases associated with undesired oxidation.

The pharmaceutical compositions which contain a statin, provided by this invention, can be formulated in any pharmaceutical dosage form suitable for its administration by the chosen route of administration, e.g., oral, parenteral (subcutaneous, intramuscular, intravenous, intraperitoneal route, etc.), topical, rectal route, etc. By way of a non-limiting illustration, the pharmaceutical compositions provided by this invention can be formulated in a solid pharmaceutical dosage form administered by the oral route (e.g., granules, tablets, capsules, etc.), in a liquid pharmaceutical dosage form administered by the oral route (e.g., solutions, suspensions, emulsions, etc.), in a pharmaceutical dosage form administered by the parenteral route (e.g., solutions, suspensions, emulsions, etc.). To that end, in each case, the suitable pharmaceutically acceptable vehicles and excipients will be chosen for the selected pharmaceutical dosage form and route of administration, for example, binding agents, diluents, disintegrating agents, lubricants, wetting agents, etc., for the formulation of solid pharmaceutical dosage forms, and buffers, surfactants, etc., for the formulation of liquid pharmaceutical dosage forms. Said vehicles and excipients must be pharmaceutically acceptable and pharmacologically tolerable and have to be able to be combined with other components of the formulation without exerting any adverse effect on the subject treated. Information on said vehicles and excipients, as well as on said pharmaceutical dosage forms of said active ingredient can be found in Galenic Pharmacy treatises. A review of the different pharmaceutical dosage forms of drugs, in general, and of their methods of preparation can be found in the book "Tratado de Farmacia Galénica", by C. Fauli i Trillo, $1^{st}$ Edition, 1993, Luzán 5, S. A. de Ediciones.

The pharmaceutical composition provided for this invention comprises at least one statin in a therapeutically efficient amount. In the sense used in this description, the expression "therapeutically effective amount" relates to the amount of statin calculated to cause the desired effect. The dose of statin to be administered to a subject can vary within a wide range depending on a number of factors, including the characteristics of the compound used, e.g., its biological half-life and activity, the concentration of the statin in the pharmaceutical composition, the clinical situation of the subject, the severity of the pathology, the chosen pharmaceutical dosage form, etc. The pharmaceutical composition provided by this invention can be administered one or more times a day for preventive or therapeutic purposes or with other administration regimens, not necessarily daily but also at precise times, weekly, etc.

If desired, the pharmaceutical composition provided by this invention can be used together with other drugs, for example, drugs useful in the treatment of epilepsy, epileptic seizures, convulsions, neurodegenerative diseases, or diseases associated with undesired oxidation, for the purpose of increasing the efficacy of the pharmaceutical composition provided by this invention, a combination therapy thus being generated. Said additional drugs can form part of the same pharmaceutical composition or, alternatively, can be provided as a separate pharmaceutical composition for its administration at the same time (simultaneous administration) as the pharmaceutical composition provided by this invention or at different times (sequential administration) with respect to the administration of the pharmaceutical composition provided by this invention.

In another aspect, the invention relates to a statin for the treatment and/or prevention of epilepsy, epileptic seizures, convulsions, neurodegenerative diseases, or diseases associated with undesired oxidation. The characteristics of the statin as well as those of said diseases have already been mentioned above.

In another aspect, the invention relates to a method for the prevention and/or treatment of epilepsy, epileptic seizures, convulsions, neurodegenerative diseases, or diseases associated with undesired oxidation, which comprises administrating a therapeutically efficient amount of a statin or a pharmaceutical composition provided by this invention comprising a statin to a subject in need of treatment. The characteristics of the statin as well as those of said diseases and pharmaceutical compositions comprising a statin have already been mentioned above.

The following examples serve to illustrate the invention and must not be considered as limiting thereof.

EXAMPLE 1

Antiepileptic Effect of Simvastatin Against the Action of an Excitotoxic Substance All the animals included during the experimental process were 16 week old male mice of the FVB/N strain [Taconic Farms, Inc. (www.taconic.com)]. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The animals, distributed into different groups, were intraperitoneally inoculated with 30 mg/kg of kainate (KA) dissolved in phosphate buffer saline (PBS), according to the following protocol:

seven animals were pretreated, at 24 and 0.5 hours before the inoculation with KA, with PBS by means of intraperitoneal (i.p.) injection;

six animals were pretreated, at 24 and 0.5 hours before the inoculation with KA, with simvastatin at a dose of 50 mg/kg by means of i.p. injection; and four animals were pretreated, at 24 and 0.5 hours before the inoculation with KA, with DNQX (a specific inhibitor of KA receptors) at a dose of 30 mg/kg, by means of i.p. injection.

After the inoculation with KA, the animals were individually housed in cages to monitor them. The maximum epilepsy level of the animals was recorded every 10 minutes during the observation according to the Racine scale and for at least 120 minutes post-inoculation (m.p.i.).

Comparative studies of the epilepsy levels between the treatment with PBS, with simvastatin or with DNQX were subsequently conducted. Differences were observed in the time of the onset of the first convulsion (latency), which was greater in the case of the treatment with simvastatin (50.0±11.8 min) than in the rest of the treatments (PBS: 38.6±4.0 min; DNQX: 23.3±7.6 min) as shown in FIG. 1, which demonstrates an antiepileptic or anticonvulsant effect of simvastatin.

Figure 2:
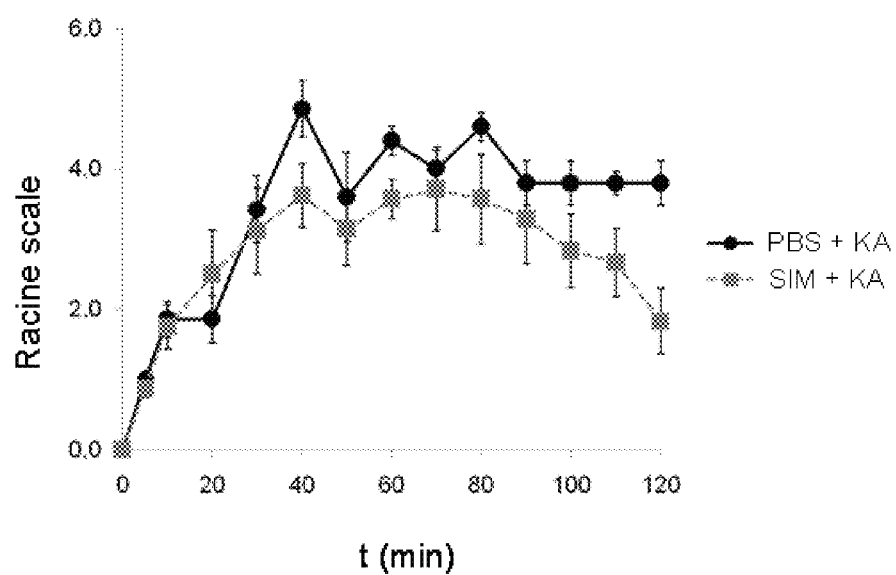
FIG. 2 is an XY scatter chart depicting the severity level of the epileptogenic score observed according to the Racine scale (Racine, Electroencephalogr Clin Neurophysiol 1972; 32[3]:281-94) versus the post-inoculation time of the epileptogenic substance (kainic acid or kainate or KA). The graph shows the evolution of the epileptogenic score of the animals according to the treatment received: PBS or simvastatin [SIM].

After 30 m.p.i., it is observed that in the treatment with PBS, the epilepsy levels exceeded level 4 of the Racine scale, which marks the onset of severe convulsions (FIG. 2). The onset of severe convulsive episodes mainly occurs in the period comprised between 40 and 80 m.p.i. The treatment with simvastatin stabilized the epileptogenic levels after 30 m.p.i., not exceeding a mean value of 4 and being lower with respect to the treatment with PBS at all the time points of the observation, which demonstrates an antiepileptic or anticonvulsant effect of simvastatin. The decrease of the epilepsy levels with the treatment with simvastatin is precisely greater in the highest severity period of the convulsive episodes between 40 and 80 m.p.i., as can be observed in FIG. 2.

Figure 3:
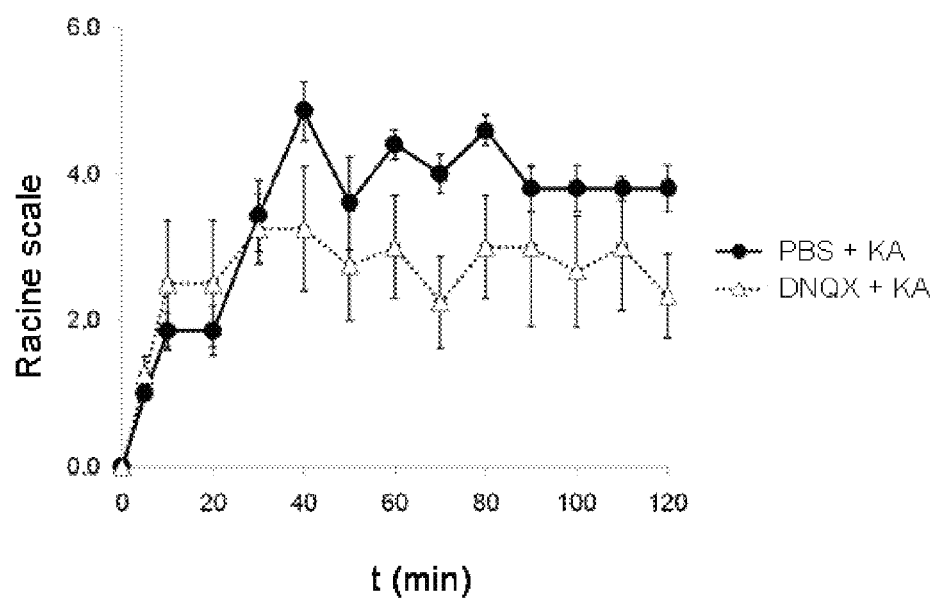
FIG. 3 is an XY scatter chart depicting the severity level of the epileptogenic score observed according to the Racine scale (Racine, Electroencephalogr Clin Neurophysiol 1972; 32[3]:281-94) versus the post-inoculation time of the epileptogenic substance (kainic acid or kainate or KA). The graph shows the evolution of the epileptogenic score of the animals according to the treatment received: PBS or DNQX (a kainate antagonist).

For the purpose of validating the observations made in the antiepileptic effect of simvastatin, the epilepsy level between mice treated with PBS was compared against DNQX (a known antagonist of KA receptors). In FIG. 3 it is observed that the treatment with DNQX prevents the increase of the epileptic levels after 30 m.p.i. of KA, showing, in a manner similar to simvastatin, a greater effect during the highest severity period of the convulsive episodes occurring between 40 and 80 m.p.i.

EXAMPLE 2

Dose Dependency in the Antiepileptic Effect of Simvastatin

Example 1 shows that the treatment with simvastatin has an antiepileptic effect against an excitotoxic aggression. Based on these results, the inventors decided to study the dependency on the dose of simvastatin in its antiepileptic effect.

All the animals included during the experimental process were 16 week old male mice of the FVB/N strain. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The animals, distributed into different groups, were intraperitoneally inoculated with 25 mg/kg of KA dissolved in PBS, according to the following protocol:
  three animals were pretreated, at 24 and 0.5 hours before the inoculation with KA, with simvastatin at a dose of 10 mg/kg by means of i.p. injection; and
  two animals were pretreated, at 24 and 0.5 hours before the inoculation with KA, with simvastatin at a dose of 50 mg/kg, by means of i.p. injection After the inoculation with KA, the animals were individually housed in cages to monitor them. The maximum epilepsy level of the animals was recorded every 10 minutes during the observation according to the Racine scale and for at least 120 minutes post-inoculation (m.p.i.).

Figure 4:
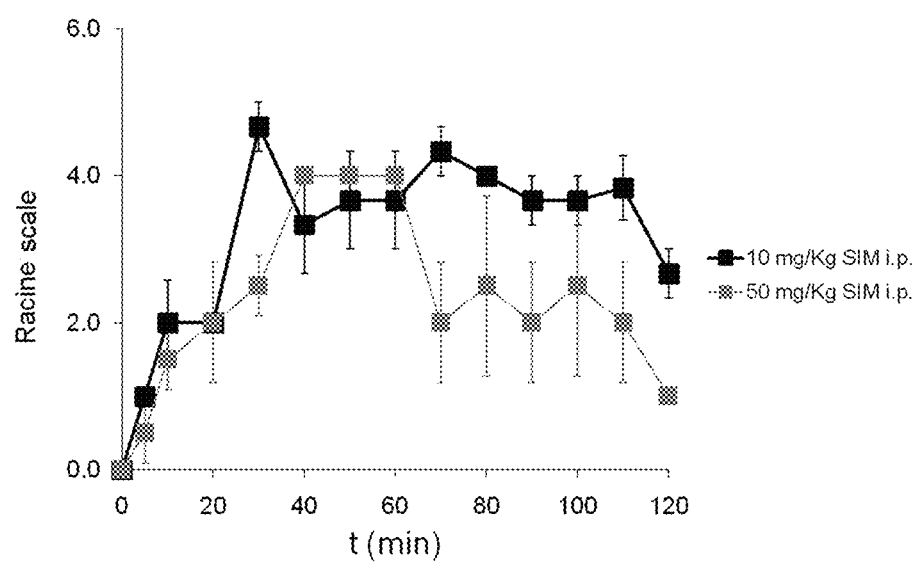
FIG. 4 is an XY scatter chart depicting the severity level of the epileptogenic score observed according to the Racine scale (Racine, Electroencephalogr Clin Neurophysiol 1972; 32[3]:281-94) versus the post-inoculation time of the epileptogenic substance (kainic acid or kainate or KA). The graph shows the evolution of the epileptogenic score of the animals according to the dose of simvastatin (SIM) administered during the treatment.

A lower epilepsy level is generally observed in the mice treated with 50 mg/kg of simvastatin versus those treated with 10 mg/kg of simvastatin during the observation period (FIG. 4). Outstandingly, a drastic difference is observed after 60 m.p.i., which shows that the use of a higher dose of simvastatin produces a lower epilepsy rate and favors the recovery of the animals more quickly than low doses. With these results the dose dependency in the antiepileptic effect of simvastatin is shown.

EXAMPLE 3

Effect of the Route of Administration on the Antiepileptic Effect of Simvastatin As shown in Examples 1 and 2, simvastatin has antiepileptic properties and such properties depend on the dose at which said compound is administered. Due to these observations, the inventors decided to investigate if the antiepileptic effect of simvastatin would also be modulated by the route of administration. All the animals included during the experimental process were 16 week old male mice of the FVB/N strain. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The animals, distributed into different groups, were intraperitoneally inoculated with 25 mg/kg of KA dissolved in PBS, according to the following protocol:
  three animals were pretreated, at 24 and 0.5 hours before the inoculation with KA, with simvastatin at a dose of 50 mg/kg by means of direct oral administration; and
  two animals were pretreated, at 24 and 0.5 hours before the inoculation with KA, with simvastatin at a dose of 50 mg/kg by means of i.p. injection After the inoculation with KA, the animals were individually housed in cages to monitor them. The maximum epilepsy level of the animals was recorded every 10 minutes during the observation according to the Racine scale and for at least 120 minutes post-inoculation (m.p.i.).

Figure 5:
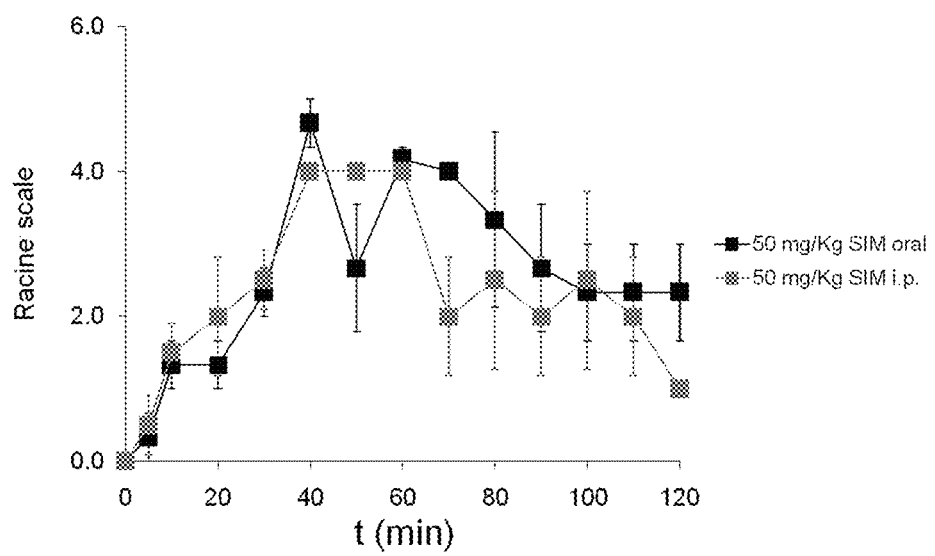
FIG. 5 is an XY scatter chart depicting the severity level of the epileptogenic score observed according to the Racine scale (Racine, Electroencephalogr Clin Neurophysiol 1972; 32[3]:281-94) versus the post-inoculation time of the epileptogenic substance (kainic acid or kainate or KA). The graph shows the evolution of the epileptogenic score of the animals according to the route of administration of simvastatin (SIM) used during the treatment.

A decrease of the epilepsy levels is generally observed after 40 m.p.i. in both groups of animals (FIG. 5). This result shows the efficacy of simvastatin as an antiepileptic by means of both types of administration. It is also observed that the decrease of the severity in the convulsive episodes is quicker by means of the i.p. injection than by means of the direct oral administration. In FIG. 5 it can be observed how the i.p. administration decreases the epileptic levels to level 2 according to the Racine scale at 70 m.p.i. and to level 1 at 120 m.p.i., whereas the oral administration does not reach level 2 until 100 m.p.i. and maintains that level until 120 m.p.i. These results show that the route of administration affects the efficacy of simvastatin as an antiepileptic compound.

EXAMPLE 4

Protective Effect of Simvastatin Against Death Caused by an Excitotoxic Substance As shown in Examples 1, 2 and 3, simvastatin has antiepileptic and anticonvulsant properties. The severity of the convulsions and the chain effect of excitotoxicity induces, in some cases, the death of the animal. Due to this, the inventors decided to investigate if the antiepileptic effect of simvastatin was accompanied by a reduction of the mortality caused by an excitotoxic substance.

All the animals included during the experimental process were 16 week old male mice of the FVB/N strain. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The animals, distributed into different groups, were intraperitoneally inoculated with 30 mg/kg of KA dissolved in PBS, according to the following protocol:
  seven animals were pretreated, at 24 and 0.5 hours before the inoculation with KA, with PBS by means of i.p. injection, and, subsequently, after the inoculation with KA, they were treated daily with PBS until 7 days post-inoculation (d.p.i.); and
  six animals were pretreated, at 24 and 0.5 hours before the inoculation with KA, with simvastatin at a dose of 50 mg/kg by means of i.p. injection, and, subsequently, after the inoculation with KA, they were treated daily with simvastatin at a dose of 50 mg/kg until 7 d.p.i.

After the inoculation with KA and, once the observation period was considered to be concluded after 150 m.p.i. of KA, the animals were housed in individual cages for their treatment with PBS, or with a dose of 50 mg/kg of a suspension of simvastatin in PBS, for the period of 7 d.p.i. The deaths were recorded in that time period.

Figure 6:
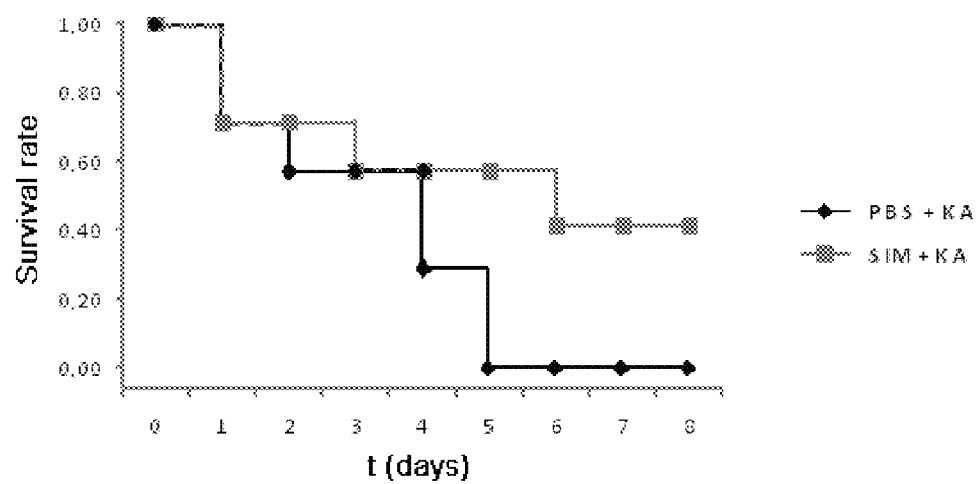
FIG. 6 is a Kaplan-Meier graph showing the survival index of the mice treated with PBS and with kainate [KA] and the comparison thereof with the mice treated with simvastatin [SIM] and with KA.

FIG. 6 shows the results by means of a survival curve. That figure shows a higher survival rate in the mice which were treated with simvastatin with respect to those treated with PBS. These mortality results indicate that the treatment with simvastatin protected the animals from death due to convulsions and to the rest of the organic effects caused by an excitotoxic substance.

EXAMPLE 5

Protective Effect of Simvastatin Against Neuronal Death in the Hippocampus Caused by an Excitotoxic Substance As shown in Examples 1, 2 and 3, simvastatin has antiepileptic properties. Furthermore, as shown in Example 4, simvastatin reduces the mortality due to the effect of an excitotoxic substance. In addition, the severity in the epileptic symptoms has a direct correlation with neuronal death and the destructuring of specific regions (e.g., the hippocampus). Due to this, the inventors decided to investigate if the antiepileptic and protective effect of simvastatin was accompanied by a reduction of these effects at cell level caused by an excitotoxic substance.

All the animals included during the experimental process were 16 week old male mice of the FVB/N strain. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The animals, distributed into different groups, were intraperitoneally inoculated with 30 mg/kg of KA dissolved in PBS, or with PBS (control), according to the following protocol:
seven animals were pretreated, at 24 and 0.5 hours before the inoculation with KA, with PBS by means of i.p. injection, and, subsequently, after the inoculation with KA, they were treated daily with PBS until 7 d.p.i.;
six animals were pretreated, at 24 and 0.5 hours before the inoculation with KA, with simvastatin at a dose of 50 mg/kg by means of i.p. injection, and, subsequently, after the inoculation with KA, they were treated daily with simvastatin at a dose of 50 mg/kg, until 7 d.p.i.; and
five animals were inoculated with PBS (instead of KA) by means of i.p. injection, and were pretreated with PBS, at 24 and 0.5 hours before the inoculation with PBS, by means of i.p. injection, and they were subsequently treated daily with PBS until 7 days d.p.i.

After the inoculation with KA (or with PBS), the animals were housed in individual cages for their treatment with PBS or with a dosage of 50 mg/kg of a suspension of simvastatin in PBS for a period of 7 days. Once that time period of 7 days of treatment had concluded, the animals were sacrificed and their brains were dissected. The brain samples were processed and included in paraffin. Hematoxylin and eosin stain was used in 5 μm thick sections to analyze the cell architecture of the hippocampus.

Figure 7:
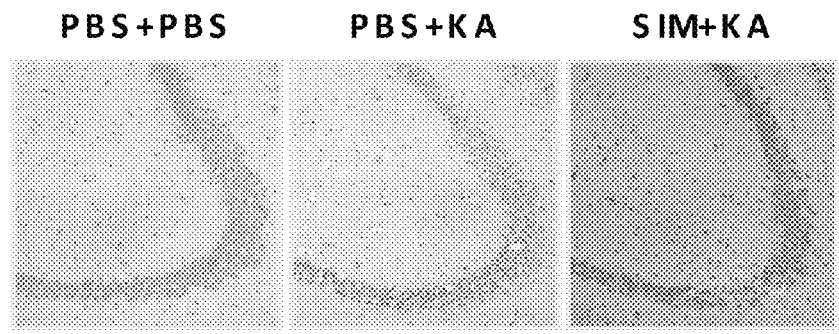
FIG. 7 is a micrograph composition showing a region of the hippocampus stained with hematoxylin & eosin of mice treated with PBS and PBS, mice treated with PBS and with kainate [KA] and mice treated with simvastatin [SIM] and with KA.

FIG. 7 shows the cell death foci wherein the necrotic nuclei (small dots with an intense color) and/or the degenerating cells (pycnotic nuclei with a more reduced size than the normal one and with a more intense color) are located. Both in the group of animals treated with PBS and KA (PBS+KA) and in the group of animals treated with simvastatin and KA (SIM+KA), there is evidence of neuronal death in the hippocampus. The fundamental difference lied in the fact that the affected areas in the group of animals treated with simvastatin are restricted to the CA2 region, whereas the group of animals treated with PBS shows a more general destructuring of the hippocampus, evidence of neuronal death in CA1, CA2, CA3 and dentate gyrus being observed. These results showed the capacity of simvastatin to minimize the effects of neuronal damaged caused by an excitotoxic substance.

EXAMPLE 6

Neuroprotective Effect of Simvastatin Against the Neurodegeneration Caused by an Excitotoxic Substance As shown in Example 5, simvastatin prevents the destructuring and neuronal death in the hippocampus due to the effect of a neurotoxic substance. For the purpose of better defining the neuroprotective effect which was observed in Example 5, the inventors decided to study the neurodegenerative process which was occurring in the neurons of the hippocampus and the effect that the treatment with simvastatin had thereon.

All the animals included during the experimental process were 16 week old male mice of the FVB/N strain. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The animals, distributed into different groups, were intraperitoneally inoculated with 30 mg/kg of KA dissolved in PBS, or with PBS (control), according to the following protocol:
seven animals were pretreated, at 24 and 0.5 hours before the inoculation with KA, with PBS by means of i.p. injection, and, subsequently, after the inoculation with KA, they were treated daily with PBS until 7 d.p.i.;
six animals were pretreated, at 24 and 0.5 hours before the inoculation with KA, with simvastatin at a dose of 50 mg/kg by means of i.p. injection, and, subsequently, after the inoculation with KA, they were treated daily with simvastatin at a dose of 50 mg/kg, until 7 d.p.i.; and
five animals were inoculated with PBS (instead of KA) by means of i.p. injection, and were pretreated with PBS, at 24 and 0.5 hours before the inoculation with PBS, by means of i.p. injection, and they were subsequently treated daily with PBS until 7 days d.p.i.

After the inoculation with KA (or with PBS), the animals were housed in individual cages for their treatment with PBS or with a dose of 50 mg/kg of a suspension of simvastatin in PBS for a period of 7 days. Once that time period of 7 days of treatment had concluded, the animals were sacrificed and their brains were dissected. The brain samples were processed and included in paraffin. The fluorescent Fluoro Jade B stain was used in 5 μm thick sections to analyze the neurodegeneration of the hippocampus. This staining labels the neurons which are in a degenerative process.

Figure 8:
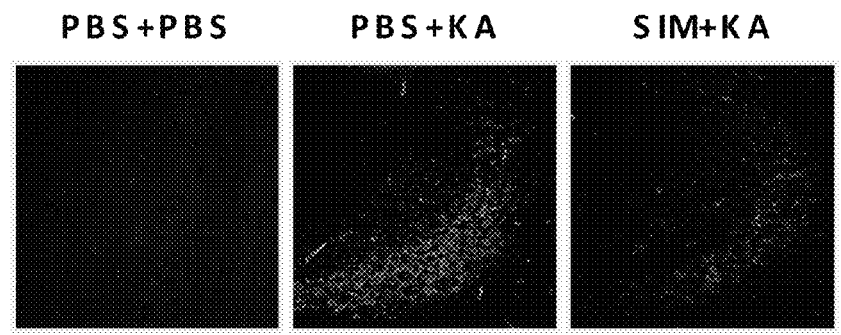
FIG. 8 is a micrograph composition showing a region of the hippocampus stained with Fluoro Jade B of mice treated with PBS and PBS, mice treated with PBS and with kainate [KA] and mice treated with simvastatin [SIM] and with KA.

In FIG. 8 it is observed that the treatment with simvastatin (SIM+KA) qualitatively reduces the number of degenerating neurons of the hippocampus and the intensity of the labeling with Fluoro Jade B. These results showed the neuroprotective capacity of simvastatin against the action of an excitotoxic substance.

EXAMPLE 7

Neuroprotective Effect of Simvastatin Against the Apoptosis Caused by an Excitotoxic Substance As shown in Examples 5 and 6, simvastatin has a neuroprotective effect on the hippocampus against the effect of a neurotoxic substance. For the purpose of determining the protective capacity of simvastatin against the death by apoptosis, the inventors decided to study the effect of the treatment with simvastatin on neuronal death by apoptosis in the neurons of the hippocampus caused by an excitotoxic substance.

All the animals included during the experimental process were 16 week old male mice of the FVB/N strain. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The animals, distributed into different groups, were intraperitoneally inoculated with 30 mg/kg of KA dissolved in PBS, or with PBS (control), according to the following protocol:

seven animals were pretreated, at 24 and 0.5 hours before the inoculation with KA, with PBS by means of i.p. injection, and, subsequently, after the inoculation with KA, they were treated daily with six animals were pretreated, at 24 and 0.5 hours before the inoculation with KA, with simvastatin at a dose of 50 mg/kg by means of i.p. injection, and, subsequently, after the inoculation with KA, they were treated daily with simvastatin at a dose of 50 mg/kg, until 7 d.p.i.; and five animals were inoculated with PBS (instead of KA) by means of i.p. injection, and were pretreated with PBS, at 24 and 0.5 hours before the inoculation with PBS, by means of i.p. injection, and they were subsequently treated daily with PBS until 7 days d.p.i.

After the inoculation with KA (or with PBS), the animals were housed in individual cages for their treatment with PBS or with a dose of 50 mg/kg of a suspension of simvastatin in PBS for a period of 7 days. Once that time period of 7 days of treatment had concluded, the animals were sacrificed and their brains were dissected. The brain samples were processed and included in paraffin. The fluorescent Acridine Orange staining was used in 5 μm thick sections to analyze the neuronal death by apoptosis in the hippocampus. This staining labels the single-stranded DNA which is produced as a consequence of the apoptotic process.

Figure 9:
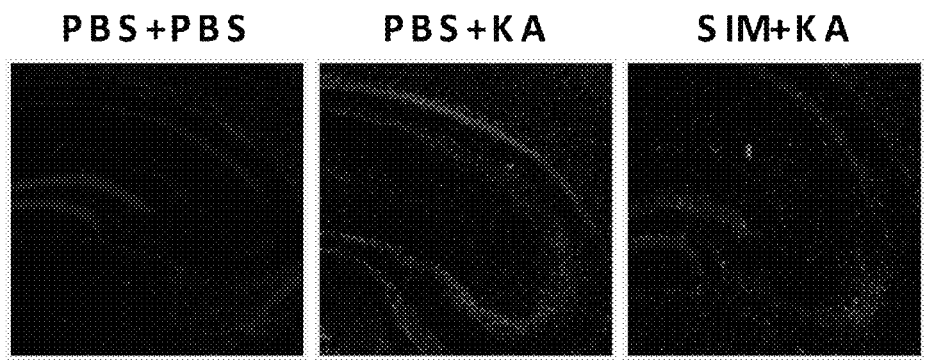
FIG. 9 is a micrograph composition showing a region of the hippocampus stained with Acridine Orange of mice treated with PBS and PBS, mice treated with PBS and with kainate [KA] and mice treated with simvastatin [SIM] and with KA.

In FIG. 9 it is observed that the treatment with simvastatin qualitatively reduces the number of neurons in apoptosis. Furthermore, the positive labeling for apoptosis in the group of animals treated with simvastatin (SIM+KA) is exclusively restricted to the CA2 region of the hippocampus. However, the group of animals treated with PBS (PBS+KA) shows, in a more numerous manner, neurons in apoptosis in the CA1, CA2, CA3 and dentate gyrus regions. These results demonstrated the protective capacity of simvastatin against neuronal death by apoptosis caused by the administration of an excitotoxic substance.

EXAMPLE 8

Neuroprotective Effect of Simvastatin Against Reactive Gliosis Caused by an Excitotoxic Substance As shown in Examples 5, 6 and 7, simvastatin has a direct neuroprotective effect on neurodegeneration and on neuronal death in the hippocampus against the effect of a neurotoxic substance. For the purpose of determining if the protective capacity of simvastatin had a global effect, the inventors decided to study other histopathological labels indicating neuronal damage. To that end, the reactive gliosis caused in the hippocampus by an excitotoxic substance and the effect that the treatment with simvastatin had thereon was analyzed.

All the animals included during the experimental process were 16 week old male mice of the FVB/N strain. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The animals, distributed into different groups, were intraperitoneally inoculated with 30 mg/kg of KA dissolved in PBS, or with PBS (control), according to the following protocol:

seven animals were pretreated, at 24 and 0.5 hours before the inoculation with KA, with PBS by means of i.p. injection, and, subsequently, after the inoculation with KA, they were treated daily with PBS until 7 d.p.i.;

six animals were pretreated, at 24 and 0.5 hours before the inoculation with KA, with simvastatin at a dose of 50 mg/kg by means of i.p. injection, and, subsequently, after inoculation with KA, they were treated daily with simvastatin at a dose of 50 mg/kg, until 7 d.p.i.; and KA) by means of i.p. injection, and were pretreated with PBS, at 24 and 0.5 hours before the inoculation with PBS, by means of i.p. injection, and they were subsequently treated daily with PBS until 7 days d.p.i.

After the inoculation with KA (or with PBS), the animals were housed in individual cages for their treatment with PBS or with a dose of 50 mg/kg of a suspension of simvastatin in PBS for a period of 7 days. Once that time period of 7 days of treatment had concluded, the animals were sacrificed and their brains were dissected. The brain samples were processed and included in paraffin. The fluorescence immunohistochemistry against the glial fibrillary acidic protein (GFAP) was used to analyze reactive gliosis in the hippocampus. The activation of the astrocytes which show a higher intensity of the labeling of this protein and increase in number as a response to neuronal damage is detected by means of this technique.

Figure 10:
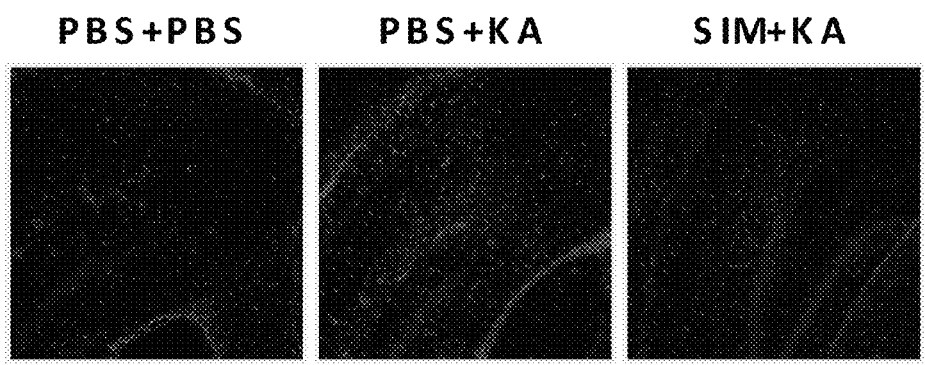
FIG. 10 is a micrograph composition showing a region of the hippocampus labeled against the glial fibrillary acidic protein (GFAP) of mice treated with PBS and PBS, mice treated with PBS and with kainate [KA] and mice treated with simvastatin [SIM] and KA.

In FIG. 10 it is observed that the administration of an excitotoxic substance and the treatment with PBS causes an astrocytic activation in the neuropil of the hippocampus (PBS+KA). However, the treatment with simvastatin qualitatively reduces this activation and the presence of astrocytes in this region of the hippocampus (SIM+KA). These results, together with those obtained in Examples 5, 6 and 7 demonstrate the neuroprotective capacity of simvastatin against the effects of the administration of an excitotoxic substance.

EXAMPLE 9

Antioxidant Effect of Simvastatin Against the Lipid Peroxidation Caused by an Excitotoxic Substance For the purpose of determining if the neuroprotective capacity of simvastatin also included an antioxidant effect, the inventors decided to study the effect that the treatment with simvastatin had on the lipid peroxidation induced by an excitotoxic substance.

All the animals included during the experimental process were 16 week old male mice of the FVB/N strain. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The animals, distributed into different groups, were intraperitoneally inoculated with 30 mg/kg of KA dissolved in PBS, or with PBS (control), according to the following protocol:
- seven animals were pretreated, at 24 and 0.5 hours before the inoculation with KA, with PBS by means of i.p. injection, and, subsequently, after the inoculation with KA, they were treated daily with PBS until 7 d.p.i.;
- six animals were pretreated, at 24 and 0.5 hours before the inoculation with KA, with simvastatin at a dose of 50 mg/kg by means of i.p. injection, and, subsequently, after inoculation with KA, they were treated daily with simvastatin at a dose of 50 mg/kg, until 7 d.p.i.; and
- five animals were inoculated with PBS (instead of KA) by means of i.p. injection, and were treated with PBS, at 24 and 0.5 hours before the inoculation with PBS, by means of i.p. injection, and, they were subsequently treated daily with PBS until 7 days d.p.i.

After the inoculation with KA (or with PBS), the animals were housed in individual cages for their treatment with PBS or with a dose of 50 mg/kg of a suspension of simvastatin in PBS for a period of 7 days. Once that time period of 7 days of treatment had concluded, the animals were sacrificed and their brains were dissected. The brain samples were processed and included in paraffin. The bright-field immunohistochemistry against 4-hydroxynonenal (HNE), which allows detecting the Michael adducts produced by this type of oxidative damage, was used to analyzed the lipid peroxidation.

Figure 11:
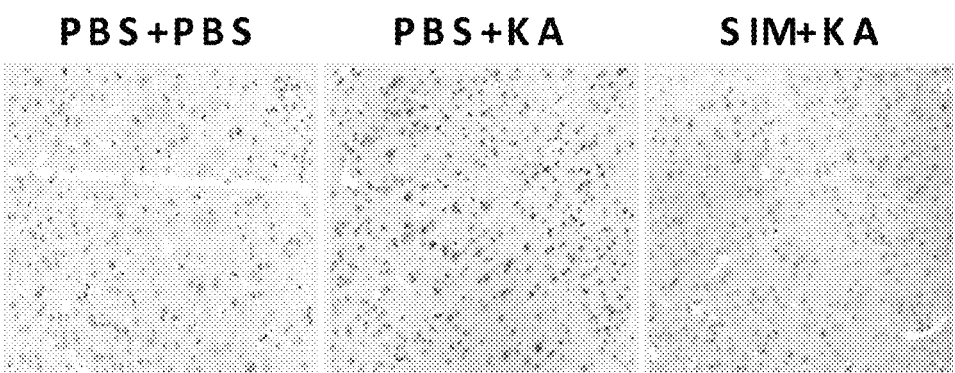
FIG. 11 is a micrograph composition showing a region of the hippocampus labeled against HNE of mice treated with PBS and PBS, mice treated with PBS and with kainate [KA] and mice treated with simvastatin [SIM] and KA.

In FIG. 11 it is observed that the administration of an excitotoxic substance (KA) and the treatment with PBS shows an HNE labeling in pyramidal neurons of the sensorimotor cortex region (PBS+KA). However, the treatment with simvastatin qualitatively reduces the number of labeled neurons and the intensity of the HNE signal (SIM+KA). These results show that simvastatin, in addition to a neuroprotective effect on the neurons of the hippocampus, has an antioxidant effect in cerebral cortex regions since it prevents the oxidative damage by lipid peroxidation due to the action of an excitotoxic substance.

EXAMPLE 10

Antiepileptic Effect of Lovastatin Against the Action of an Excitotoxic Substance All the animals included during the experimental process were 12 week old male mice of the FVB/N strain [Taconic Farms, Inc. (www.taconic.com)]. The experiments were carried out strictly following the *Guidance on the Operation of Animals* (Scientific Procedures, Act. 1986). The animals had their respective quarantine period and were treated with maximum precaution to minimize possible contaminations during inoculations and handling.

The mice, distributed into different groups, were intraperitoneally inoculated with 25 mg/kg of KA dissolved in PBS, according to the following protocol:
- five mice were pretreated, at 24 and 0.5 hours before the inoculation with KA, with PBS by means of intraperitoneal (i.p.) injection; and
- five animals were pretreated, at 24 and 0.5 hours before the inoculation with KA, with lovastatin at a dose of 50 mg/kg by means of i.p. injection After the inoculation with KA, the animals were individually housed in cages to monitor them. The maximum epilepsy level of the animals was recorded every 10 minutes during the observation according to the Racine scale and for at least 120 minutes post-inoculation (m.p.i.). Comparative studies of the epilepsy levels between the treatment with PBS and with lovastatin (FIG. 12) were subsequently conducted. After the inoculation of KA, there was an increase of the epilepsy levels until the period of 50-60 m.p.i., in which the first convulsive episodes started to occur in both groups of mice. After that time, a progressive decrease was observed in the severity of the symptoms of the group treated with lovastatin, unlike the group to which PBS had been administered, in which the epileptic levels continued to increase until 90 m.p.i. The treatment with lovastatin completely reduced the epilepsy symptoms caused by KA at the end of the observation time, whereas the PBS+KA group maintained levels of about 3 at the end of the experiment. The difference between both symptom kinetics was statistically significant (analysis of variance: $F(1.28)=14.97$; p-value=0.00059).

Differences were additionally observed between the treatments in the entrance into status epilepticus, defined as the presence of tonic and/or clonic convulsions in a continuous manner for at least 30 minutes. The treatment with lovastatin completely protected from the entrance into status epilepticus after the inoculation of KA (0 of 5 mice), whereas in the mice to which PBS had been administered the entrance into status epilepticus occurred in 60% of the cases (3 of 5).

The invention claimed is:
1. A method for the prevention and/or treatment of:
a) epilepsy, or
b) epileptic seizures,
in a subject in need thereof, said method comprising administering to said subject a therapeutically effective amount of a semivastatin or the pharmaceutically acceptable salts thereof.

* * * * *

UNITED STATES PATENT AND TRADEMARK OFFICE
CERTIFICATE OF CORRECTION

PATENT NO. : 8,927,599 B2  
APPLICATION NO. : 12/995816  
DATED : January 6, 2015  
INVENTOR(S) : Burgos Muñoz et al.

Page 1 of 1

It is certified that error appears in the above-identified patent and that said Letters Patent is hereby corrected as shown below:

In the Claims

Column 18; Line 48, Claim 1: change "1. A method for the prevention and/or treatment of:"
to --A method for the treatment of--

Column 18; Line 53, Claim 1: change "semivastatin or the pharmaceutically acceptable salts thereof."
to --simvastatin or the pharmaceutically acceptable salts thereof.--

Signed and Sealed this
Fifth Day of May, 2015

Michelle K. Lee
*Director of the United States Patent and Trademark Office*